United States Patent [19]

Hamel et al.

[11] Patent Number: 4,472,586
[45] Date of Patent: Sep. 18, 1984

[54] 6H-DIBENZ[B,E][1,4]OXATHIEPIN DERIVATIVES

[75] Inventors: Pierre Hamel, Vimont; Joshua Rokach, Laval, both of Canada

[73] Assignee: Merck Frosst Canada, Inc., Kirkland, Canada

[21] Appl. No.: 520,053

[22] Filed: Aug. 5, 1983

Related U.S. Application Data

[63] Continuation-in-part of Ser. No. 429,577, Sep. 30, 1982, abandoned.

[51] Int. Cl.³ .......................................... C07D 327/02
[52] U.S. Cl. ...................................... 549/10; 424/276
[58] Field of Search .......................................... 549/10

[56] References Cited

U.S. PATENT DOCUMENTS 4,237,160 12/1980 Hamel et al. ..................... 424/275
4,282,365 8/1981 Rokach et al. .................... 548/252

FOREIGN PATENT DOCUMENTS 80301811 1/1981 European Pat. Off. .

Primary Examiner—Richard Raymond
Attorney, Agent, or Firm—Julian S. Levitt; Hesna J. Pfeiffer; Paul H. Ginsburg

[57] ABSTRACT

Novel 6H-dibenz[b,e][1,4]oxathiepin derivatives of the formulae I and IA are employed in the treatment and control of allergic conditions such as allergic asthma.

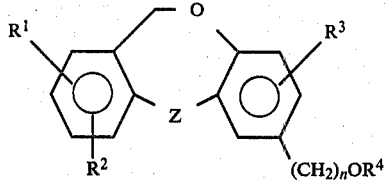

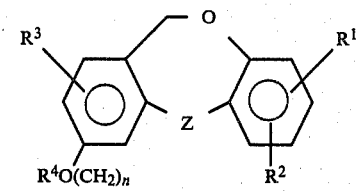

9 Claims, No Drawings

6H-DIBENZ[B,E][1,4]OXATHIEPIN DERIVATIVES

CROSS REFERENCE TO RELATED APPLICATION

This application is a continuation-in-part of copending application, U.S. Ser. No. 429,577, filed Sept. 30, 1982, now abandoned.

SUMMARY OF THE INVENTION

This invention relates to prostaglandin antagonists useful in treating a variety of conditions, such as allergic asthma where excessive contractile activity of prostaglandins and prostaglandin biosynthetic intermediates occur. These prostaglandin antagonists are a novel group of 6H-dibenz[b,e][1,4]oxathiepins having the following structural formulae:

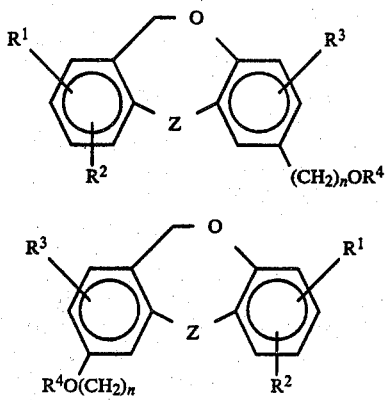

wherein
n is an integer of from 1-4;
Z is thio, sulfinyl, or sulfonyl;
$R^1$, $R^2$ and $R^3$ are each independently selected from hydrogen, halogen, amino, $C_1$ to $C_4$ alkyl, $C_1$ to $C_4$ alkylthio, $C_1$ to $C_4$ alkylsulfinyl, $C_1$ to $C_4$ alkylsulfonyl, trifluoromethyl, trifluoromethylthio, cyano, nitro, and $C_1$ to $C_4$ alkyl or dialkylamino, $C_1$ to $C_4$ alkoxy, $C_1$ to $C_4$ alkanoyl, aralkyl, or hydroxy $C_1$ to $C_4$ alkyl;
$R^4$ is H, $C_1$ to $C_4$ acyl, $C_1$ to $C_4$ alkylaminoacyl, $C_1$ to $C_4$ alkylcarboxy, $C_1$ to $C_4$ alkylcarboxamido, $C_1$ to $C_4$ alkylcarboxamidoacyl or $C_1$ to $C_4$ acyloxy $C_1$ to $C_4$ alkyl;
$R_1$ and $R_2$ can also be a $C_2$ to $C_6$ polymethylene chain optionally with a hydroxy or keto functionality.

As used herein, the term halogen (or halo) includes chlorine, bromine, iodine, and fluorine. Unless otherwise specifically stated, the terms $C_1$ to $C_4$ alkyl, $C_1$ to $C_4$ acyl and $C_1$ to $C_4$ alkoxy include straight and branched chain alkyl, acyl and alkoxy groups having 1 to 4 carbon atoms in the alkyl, acyl or alkoxy moiety such as, for example, methyl, ethyl, n-propyl, isopropyl, n-butyl, methoxy, ethoxy, n-propoxy, and isobutoxy, substituted alkyl groups such as hydroxy alkyl may have the substituent at any position and include, for example, hydroxymethyl, 2-hydroxyethyl, 2-hydroxypropyl and the like. The term $C_1$ to $C_4$ alkanoyl includes straight or branched chain alkanoyl groups having 1 to 4 carbon atoms in the alkanoyl moiety such as, for example, formyl, acetyl, propanoyl, and isobutyryl. The terms aralkyl includes straight or branched chain $C_1$ to $C_4$ alkyl radicals having one of the hydrogens replaced by a phenyl or substituted phenyl group including phenyl, halophenyl such as chloro, bromo, iodo, and fluorophenyl, nitrophenyl, aminophenyl, hydroxyphenyl, loweralkylphenyl, and the like. Aralkyl groups include benzyl, phenethyl, triphenylmethyl and the like.

These dibenzoxathiepin derivatives antagonize the actions of contractile prostaglandins, such as $PGF_{2\alpha}$, $PGH_2$, and $TXA_2$. The use of agents which act as prostaglanding antagonists offers new approaches to therapy in a number of disease states. For example, certain prostaglandins, such as $PGF_{2\alpha}$, PGG, and $PGH_2$, are potent contractants of bronchial muscle. Indeed human asthmatics have been shown to be especially sensitive to the bronchial constricting action of $PGF_{2\alpha}$.

In addition to the involvement of contractile prostaglandins in chronic obstructive lung disease (or asthma), prostaglandins are known to play a role in other allergic conditions, as well as inflammation, diarrhea, hypertension, angina, platelet aggregation, cerebral spasm, premature abortion, and dismenorrhea.

In addition to the prostaglandin antagonist actions, the dibenzoxathiepins of this invention are antagonists of slow reacting substance of anapnylaxis (SRS-A). This contractile substance is released in the lung tissue in allergic asthma, and antagonism of its actions contributes to alleviation of this disease.

Tne dibenzoxathiepins of formula I of this invention are prepared according to the following general reaction scheme:

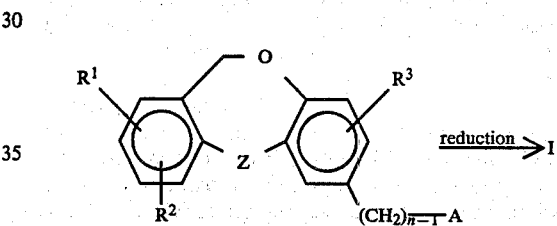

where $R^1$, $R^2$, $R^3$, Z and n are as defined above; and A is COOH or a p-$NO_2$ benzyl or loweralkyl ester thereof. IA is prepared similarly using the appropriate starting material.

As shown in the above reaction scheme, an appropriately substituted aibenzoxathiepin-2-carboxylic acid, loweralkyl ester thereof or the anhydride thereof is reduced to the correspondingly substituted 2-hydroxymethyldibenzoxathiepin by treatment with an alkali metal aluminum hydride, such as lithium aluminum hydride, diborane, or, alkali metal borohydrides, or alkali metal boro deuterides, such as $NaBH_4$. Each reagent is effective for bringing about the desired reduction to a hydroxymethyl substituent but diborane is preferred for the reduction of the carboxyl function in a dibenzothiepin-2-carboxylic acid-11,11-dioxide. The reduction is conducted in a solvent which is inert under the reaction conditions and may be either a volatile or non-volatile ether. Ethyl ether or other loweralkyl ethers are satisfactory and tetrahydrofuran is a commonly preferred solvent.

The chosen reducing reagent is employed in a slight excess over the stoichiometric amount needed in order to insure completeness of reaction. The reduction reaction is maintained at a temperature between 0° and 100° C. or the reflux temperature of the solvent. Most acids and esters are reduced relatively completely at room temperature (25° C.) and in a relatively short time (approximately 1 hour), and therefore the reduction is usually conducted by stirring the acid or ester for a period of from 30 minutes to 12 hours at a temperature of from 10° to 40° C. Following the completion of the reaction, the product is isolated by the addition of water and extraction into ether. The ether extract is evaporated to obtain the residual product which is recrystallized from an appropriate solvent.

Products which may be obtained directly by reduction of the appropriate acid are 2-hydroxymethyldibenzoxathiepin and 2-hydroxymethyldibenzoxathiepin-11,11-dioxide or derivatives bearing $R^1$ and $R^2$ or $R^3$. The 2-hydroxymethyl dibenzoxathiepin-11-oxide or derivatives thereof are prepared by oxidation of the corresponding 2-hydroxymethyldibenzoxathiepins with organic peroxides such as peroxy acids like m-chloroperbenzoic acid or hydrogen peroxide in acetic acid. The oxidation can be carried further, if an additional equivalent of oxidizing agent is employed, to produce the corresponding dibenzoxathiepins-11,11-dioxides. It will be apparent to one skilled in the art that variations in these preparative schemes will allow one to prepare a variety of substituted 2-hydroxymethyldibenzoxathiepins, as well as the corresponding oxathiepin-11-oxides and the oxathiepin-11,11-dioxides.

For example, 8-amino-2-hydroxymethyldibenzoxathiepin is prepared by reduction of the correspondingly substituted acid or by catalytic hydrogenation of 2-hydroxymethyl-8-nitrodibenzoxathiepin.

Particularly preferred embodiments of this invention are the compounds wherein $n=1$, $Z=$sulfonyl, $R=R^3=$hydrogen, and $R^1$ is at position 8 or 9 and is fluoro, chloro, bromo, or amino.

The starting materials, the carboxylic acids or esters, are described in copending application U.S. Ser. No. 238,097, filed Feb. 25, 1981. This case is incorporated herein by reference. In addition, preparative examples of some representative starting materials are found herein.

For type IA compounds generally, an appropriately substituted o-iodobenzoic acid is reacted with o-methoxythiophenol in the presence of copper powder and aqueous potassium hydroxide in order to obtain the corresponding 2-(o-methoxyphenylthio)benzoic acid. The reaction is carried out at reflux and usually requires 2 to 5 hours for completion. Upon recovery, the acid product may be converted into the corresponding lower alkanol ester by refluxing with a lower alkanol in the presence of a strong acid such as sulfuric acid, hydrochloric acid, trifluoroacetic acid and the like. The ester product then is treated with dichloromethyl methylether in the presence of titanium tetrachloride to form the corresponding 3-(o-carboloweralkoxyphenylthio)-4-methoxybenzaldehyde which then is demethylated with hydrogen bromide in glacial acetic acid to form the corresponding 3-(o-carboxyphenylthio)-4-hydroxybenzaldehyde. The aldehyde so produced then is treated with hydroxylamine hydrochloride in the presence of sodium formate and formic acid to form the corresponding 3-(o-carboxyphenylthio)-4-hydroxybenzonitrile which is treated with dicyclohexylcarbodiimide (DCC) to form the corresponding 2-cyano-6H-6-oxo-dibenz[b,e][1,4]oxathiepin. The 2-cyano-oxathiepin product then is treated with an alkali metal borohydride to form the corresponding 3-(o-hydroxymethylphenylthio)-4-hydroxybenzonitrile which is reacted with dicyclohexylcarbodiimide to form the desired 2-cyano-6H-dibenz[b,e][1,4]oxathiepin, which can be hydrolyzed to the carboxylic acid derivative.

Alternatively, an appropriately substituted o-mercaptobenzyl alcohol is reacted with 3-iodo-4-hydroxybenzoic acid in the presence of copper powder and aqueous potassium hydroxide in order to obtain the corresponding 3-(o-hydroxy methylphenylthio)-4-hydroxybenzoic acid. The reaction is carried out at reflux and generally requires 6 to 24 hours for completion. After isolation the acid product may be converted into the corresponding lower alkanol ester by refluxing with a lower alkanol in the presence of a strong acid such as sulfuric acid, hydrochloric acid, trifluoroacetic acid and the like. The ester product then is cyclized, for example through the use of diethyl azodicarboxylate in the presence of triphenyl phosphine, in an inert solvent, preferably an ether such as tetrahydrofuran, or through the use of a dehydrating agent such as dicyclohexyl carbodiimide, to afford the corresponding appropriately substituted 6H-dibenz[b,e][1,4]oxathiepin-2-carboxylate, which is then hydrolyzed through the action of an aqueous solution of a strong alkali such as sodium or potassium hydroxide followed by acidification to yield the corresponding carboxylic acid derivative.

To prepare type I derivatives, an appropriately substituted o-amino thiophenol is reacted with 2-chloro-4-nitrobenzoic acid in the presence of cuprous oxide in quinoline to produce the corresponding 2-(o-aminophenylthio)-4-nitrobenzoic acid. The amine function is then diazotized through the action of sodium nitrite in dilute aqueous sulfuric acid, and the diazonium salt transferred into the corresponding phenol by heating in 50% aqueous sulfuric acid. The precipitated product is collected, and transformed, preferably by the action of borane in tetrahydrofuran, into the corresponding 2-(o-hydroxyphenylthio)-4-nitrobenzyl alcohol. Compounds of this type are cyclized through the use of an appropriate dehydrating agent, such as dicyclohexyl carbodiimide to the corresponding 9-nitro-6H-dibenz[b,e][1,4]oxathiepin. The nitro function is transformed into an amine by one of several reducing agents, The reagent of choice being stannous chloride in a mixture of concentrated hydrochloric acid and tetrahydrofuran. The amino compound thus obtained is diazotized by treatment with sodium nitrite in aqueous hydrochloric acid, then transformed into the corresponding nitrile on addition of the diazonium salt to a mixture of cuprous cyanide and potassium cyanide in aqueous medium. The 9-cyano compounds thus obtained are then processed, via a combination of oxidation and hydrolysis, to the carboxylic acids having the desired oxidation state on the sulfur.

Certain prodrug derivatives ($R^4 \neq H$) of the compounds of formulae I or IA may be designed so as to be capable of regenerating a biologically active form of the compounds of formulae I or IA following metabolic transformation. Included among these prodrug derivatives are $C_1$ to $C_4$ acyl derivatives such as acetates which may be prepared by reacting a formula I or IA alcohol with an appropriate $C_1$ to $C_4$ anhydride in the presence of an organic base such as pyridine.

Other examples of prodrug derivatives include amino acid eaters of the compounds of formulae I and IA. These esters may be prepared by reacting the alcohol with an appropriate amino acid mixed anhydride. For example, a t-boc amino acid (e.g., t-boc glycine) may be reacted with ethlychloroformate in the presence of an organic base such as N-methylmorpholine in a suitable solvent such as THF. The blocked amine functionality may be liberated by action of, for example, hydrogen chloride in dichloromethane, to afford the hydrochloride salt of the amino acid ester of a compound of formula I or IA.

The oxathiepins of formulae I and IA are useful in the treatment and prophylaxis of human or warm-blooded animal disease conditions where excessive undesirable contractile activity of prostaglandins, such as $PGF_{2\alpha}$, or prostaglandin biosynthetic intermediates contribute. In particular, they are of value in the treatment and control of allergic conditions such as asthma.

The magnitude of a prophylactic or therapeutic dose of compounds of Formulae I and IA will, of course, vary with the nature and the severity of the condition to be treated and with the particular compound of formulae I and IA and its route of administration. In general, the dose range lies within the range of 0.2 mg to 100 mg per kg body weight per day.

The pharmaceutical compositions of the present invention comprise a compound of formulae I and IA as an active ingredient, and may also contain pharmaceutically acceptable carrier and optionally other therapeutic ingredients. The compositions include compositions suitable for oral, rectal, ophthalmic, pulmonary, nasal, dermal, topical or parenteral (including subcutaneous, intramuscular and intravenous) administration, although the most suitable route in any given case will depend on the nature and severity of the condition being treated and on the nature of the active ingredient. They may be conveniently presented in unit dosage form and prepared by any of the methods well known in the art of pharmacy.

For use where a composition for intravenous administration is employed, a suitable dosage range is from 0.2 to 10 mg (preferably 1 to 8 mg) of a compound of formulae I and IA per kg of body weight per day and in the case where an oral composition is employed a suitable dosage range is about, i.e., 1 to 50 mg of a compound of formulae I and IA per kg of body weight per day, preferably from 10 to 40 mg/kg.

Pharmaceutical compositions of the present invention suitable for oral administration and by inhalation in the case of asthma therapy may be presented as discrete units such as capsules, cachets or tablets each containing a predetermined amount of the active ingredient; as a powder or granules; or as a solution or a suspension in an aqueous liquid, a non-aqueous liquid, an oil-in-water emulsion or a water-in-oil liquid emulsion. Such compositions may be prepared by any of the methods of pharmacy but all methods include the step of bringing into association the active ingredient with the carrier which constitutes one or more necessary ingredients. In general, the compositions are prepared by uniformly and intimately admixing the active ingredient with liquid carriers or finely divided solid carriers or both, and then, if necessary, shaping the product into the desired presentation. For example, a tablet may be prepared by compression or moulding, optionally with one or more accessory ingredients. Compressed tablets may be prepared by compressing in a suitable machine, the active ingredient in a free-flowing form such as powder or granules, optionally mixed with a binder, lubricant, inert diluent, lubricating, surface active or dispersing agent. Moulded tablets may be made by moulding in a suitable machine, a mixture of powdered compound moistened with an inert liquid diluent. Desirably, each tablet contains from 50 mg to 500 mg of the active ingredient and each cachet or capsule contains from 50 mg to 500 mg of the active ingredient.

The best mode contemplated by applicants for carrying out their invention is illustrated in the following working examples. No limitation, however, is intended except as set forth in the appended claims.

EXAMPLE 1

9-Cyano-6H-dibenz[b,e][1,4]oxathiepin

Step A: 2-(o-Aminophenylthio)-4-nitrobenzoic acid

Heat a mixture of 466 g (3.72 moles) of 2-aminothiophenol, 250 g (1.24 moles) of 2-chloro-4-nitrobenzoic acid, 1.25 l of quinoline, 192 g (1.34 moles) of cuprous oxide and 125 ml of pyridine in an oil bath at 160°–170° C. with mechanical stirring for 90 minutes. Cool the mixture to room temperature and add 1.87 l of concentrated hydrochloric acid followed by 625 ml of water. Separate the precipitate and wash well with water. Extract the washed precipitate into boiling methanol and filter. Treat the hot filtrate with charcoal, filter and strip to dryness. Dissolve the residue in aqueous sodium hydroxide, filter and treat with charcoal. Acidify the filtrate and separate the precipitate. (Yield: 38 g).

Additional Crop: Take up the insoluble residue from the basic extraction into water, filter through celite and acidify. Separate the precipitate and dissolve in ethyl acetate. Treat with charcoal, filter and strip to dryness. (Yield: 23 g).

Step B: 2-(o-Hydroxyphenylthio)-4-nitrobenzoic acid

Suspend 10.15 g (35 mmoles) of the amino acid of Step A in 75 ml of water and add 4 ml concentrated sulfuric acid (7.36 g, 75 mmoles, 150 meq). Cool the mixture in an ice-bath and add 3.657 g (53 mmoles) of sodium nitrite in portions at 0°–5° C. Stir the suspension in the cold for 20 minutes. Add 10 g (91 mmoles) of sodium fluoroborate and stir for an additional 20 minutes. Separate the precipitated crude diazonium fluoroborate, suspend the precipitate in 250 ml of 50% sulfuric acid and heat in an oil bath at 90°–100° C. for 45 minutes. Cool the mixture and separate the precipitate. (Yield: 7.76 g).

Step C: 2-(o-Hydroxyphenylthio)-4-nitrobenzyl Alcohol

Dissolve 42 g (0.144 mole) of the acid of Step B in 575 ml of tetrahydrofuran and add dropwise 275 ml of borane (0.275 mole $BH_3$) in tetrahydrofuran (as a 1 molar solution) under a nitrogen atmosphere at room temperature. Stir at room temperature overnight. Slowly add excess water and concentrate to remove the tetrahydrofuran. Extract into ethyl acetate and add 120 g of silica gel to the ethyl acetate solution. Place the mixture atop a column of 1500 g of silica gel and elute with 20% ethyl acetate/benzene to obtain the pure diol. (m.p. 131°–133° C.).

Step D: 9-Nitro-6H-dibenz[b,e][1,4]oxathiepin

Stir 4.6 g of the diol of Step C and 17.1 g (5 molar equivalents) of dicyclohexylcarbodiimide together at 110°–115° C. for 4–5 hours. Cool the mixture, dissolve in 250 ml of tetrahydrofuran and filter. Add silica gel to the filtrate and strip to dryness. Place the residue atop a column of 310 g of silica gel and elute with 50:50 benzene/hexane. Strip to dryness to obtain the title product (m.p. 112°–113° C.).

Step E: 9-Amino-6H-dibenz[b,e][1-4]oxathiepin

Dissolve 7.92 g of the nitro compound of Step D in 150 ml of tetrahydrofuran and add 50 ml of concentrated hydrochloric acid. Place the mixture in a cold water bath and add 22.7 g (3 molar equivalents +10%) of stannous chloride dihydrate in portions. Stir at room temperature for 5½ hours. Dilute the reaction mixture with water, basify with 40% aqueous sodium hydroxide and extract with ethyl acetate. Wash the organics with water, dry and strip to dryness. (Yield: 7.22 g crude amine).

Step F: 9-Cyano-6H-dibenz[b,e][1,4]oxathiepin

Suspend 1.55 g (6.77 mmoles) of the amine of Step E in 36 ml of 1N hydrochloric acid and cool the mixture in an ice bath. Add slowly a solution of 502 mg (7.28 mmoles) of sodium nitrite in 10 ml of water, keeping the temperature at 0°-5° C. Stir the mixture in the cold for 15 minutes. Neutralize to pH 7 with aqueous sodium carbonate solution. Add the mixture slowly to a cooled mixture of 1.37 g (15.3 mmoles) of cuprous cyanide and 2.0 g (30.8 mmoles) of potassium cyanide in 50 ml of water at 0°-5° C. Recover the precipitate by filtration and wash well with water. Dissolve the precipitate in tetrahydrofuran, add silica gel and evaporate the tetrahydrofuran. Place the residue atop a silica gel column and elute with 50:50 benzene/hexane. Remove the solvent to obtain the title product. (m.p. 136°-137° C.).

EXAMPLE 2

9-Cyano-6H-dibenz[b,e][1,4]oxathiepin-11,11 dioxide

Dissolve 850 mg (3.56 mmole) of the 9-cyano-6H-dibenz[b,e][1,4]oxathiepin of Example 1 in 50 ml of methylene chloride. Add 2.3 g (11.3 mmole) of 85% m-chloroperbenzoic acid and stir at room temperature for 2 hours. Add excess calcium hydroxide and continue stirring for a few minutes. Filter the reaction mixture through celite and strip the filtrate to dryness. Chromatograph the residue on silica gel eluting with 25% ethyl acetate in benzene to obtain the title product. (m.p. 177°-179° C.).

EXAMPLE 3

6H-Dibenz[b,e][1,4]oxathiepin-9-carboxylic acid 11,11-dioxide

Reflux 435 mg of the nitrile of Example 2 in a mixture of 20 ml of 20% aqueous sodium hydroxide and 20 ml of ethanol for 2½ hours and cool to room temperature. Dilute the reaction mixture with water and remove most of the ethanol by evaporation under reduced pressure. Extract the aqueous residue with ethyl acetate. Acidify the aqueous solution, after evaporation of residual ethyl acetate, and separate the precipitate by filtration to obtain the title product. (m.p. 262°-265° C.).

EXAMPLE 4

9-Hydroxymethyl-6H-dibenz[b,e][1,4]oxathiepin-11,11-dioxide 725 mg (2.5 mmoles) of the acid prepared in Example 3, is dissolved, in 25 ml THF, and there is added 303 mg triethylamine (3 mmoles). The resulting solution is cooled in an ice and water bath, then 298 mg ethyl chloroformate (2.75 mmoles) is added slowly. Precipitation of Et₃N.HCl follows. The suspension is stirred in the cold for 5 minutes, then there was added 95 mg NaBH₄ (2.5 mmoles) and, slowly, 1 ml water. The mixture froths gently. After stirring for 1 hour in the cold, the cooling bath is removed and the mixture is allowed to warm to room temperature and is diluted with 5 ml water. The THF is evaporated away and the residual aqueous residue is extracted with EtOAc. Extracts are washed with water three times, dried and stripped to a colorless oil containing solids. Thin layer chromatography shows 4-5 spots at this stage. A sample is dissolved in THF and treated with addition of NaBH₄/H₂O and these several spots change into two; the bulk of the product is given the same treatment and after the same workup as before, the crude mixture of two products is chromatographed on silica gel, and a white solid is obtained (most polar compound) triturated in hexane and filtered to afford the title compound.

EXAMPLE 5

6H-Dibenz[b,e][1,4]oxathiepin-9-carboxylic acid

Reflux 800 mg of the nitrile of Example 1 in a mixture of 25 ml of 20% sodium hydroxide and 25 ml of ethanol for 3 hours. Cool the reaction mixture to room temperature and remove most of the ethanol by evaporation under reduced pressure. Dissolve the precipitated sodium salt by diluting with water and warming. Extract with ethyl acetate and acidify the aqueous phase. Separate the precipitate by filtration to obtain the title product. (m.p. 241°-243° C.).

EXAMPLE 6

9-Hydroxymethyl-6H-dibenz[b,e][1,4]oxathiepin

Dissolve 10 mmoles of 6H-dibenz[b,e][1,4]oxathiepin-9-carboxylic acid from Example 5 in 75 ml tetrahydrofuran, add slowly at ambient temperature 12 ml of a 1 molar solution of borane in tetrahydrofuran, stir for 3 hours, add 20 ml water, evaporate the tetrahydrofuran, dilute the residue with water and filter. Crystallize the crude product from ethanol.

EXAMPLE 7

6H-Dibenz[b,e][1,4]oxathiepin-9-carboxylic acid 11-oxide

Dissolve with warming 380 mg of the carboxylic acid of Example 5 in 38 ml of glacial acetic acid. Place the reaction mixture in an oil bath at 40° C. and, after equilibration, add 1.5 ml of 30% hydrogen peroxide. Stir the mixture at 40° C. for 3½ hours until solution clears. Dilute with 300 ml of water and separate the precipitate by filtration to obtain the title product. (m.p. 242°-245° ).

EXAMPLE 8

9-Hydroxymethyl-6H-dibenz[b,e][1,4]oxathiepin-11-oxide

Reduce 6H-dibenz[b,e][1,4]oxathiepin-9-carboxylic acid-11-oxide from Example 7 with borane in THF as in Example 6 to obtain the corresponding alcohol.

EXAMPLE 9

2-Cyano-6H-dibenz[b,e][1,4]oxathiepin

Step A: 2-(o-Methoxyphenylthio)benzoic acid

Stir under reflux for 3 hours a mixture of 70 g (0.5 mole) of o-methoxythiophenol, 120.5 g (0.486 mole) of o-iodobenzoic acid, 81.7 g (1.46 mole) of potassium hydroxide, 85 g (1.34 mole) of copper powder and 800 ml of water. Filter the reaction mixture hot and again filter the filtrate through celite. Acidify the filtrate with concentrated hydrochloric acid. Separate the precipitate, wash well with water and dry in vacuo at 70° C. to obtain the title product. (m.p. 198°14 200° C.).

Step B: Methyl 2-(o-Methoxyphenylthio)benzoate

Dissolve 115 g of the acid of Step A in 3.5 l of methanol and add slowly 25 ml of sulfuric acid. Stir under reflux for 72 hours. Cool the reaction mixture to room temperature and add 100 g of sodium bicarbonate in portions. Stir for an additional hour and strip to dryness. Dissolve the residue in methylene chloride and wash the solution three times with water. Dry the solution and strip to an oil which solidifies. (m.p. 82°–84° C.).

Step C: 3-(o-Carbomethoxyphenylthio)-4-methoxybenzaldehyde

Dissolve 117 g (0.427 mole) of the ester of Step B in 1500 ml of 1,2-dichloroethane and cool with stirring in an ice-bath. Add 200 ml (345 g, 1.82 mole) of titanium tetrachloride at a rapid dropwise rate. Add also fairly rapidly 154 g (1.34 mole) of dichloromethyl methyl ether. Stir the mixture under a nitrogen atmosphere overnight then pour into ice. After shaking, separate the organic phase and extract the aqueous phase twice with methylene chloride. Wash the combined organic phases twice with water, dry and strip to an oil which crystallizes. (m.p. 99°–104° C.).

Step D: 3-(o-Carboxyphenylthio)-4-hydroxybenzaldehyde

Heat 126 g of the aldehyde of Step C in a mixture of 1500 ml of glacial acetic acid and 1500 ml of 48% hydrogen bromide in an oil bath at 150° C. with mechanical stirring until no trace of non-demethylated product remains (4–5 days). Cool the reaction mixture and pour into 7 l of water. Separate the precipitate, wash well with water and dry in vacuo at 70° C. to constant weight. (Yield: 108.2 g).

Step E: 3-(o-Carboxyphenylthio)-4-hydroxybenzonitrile

Reflux 91.3 g of the aldehyde of Step D, 27.4 g of hydroxylamine hydrochloride and 41.9 g of sodium formate in 900 ml of formic acid (98–100%) for 1¼ hours. Cool the mixture and pour into 2½ l. of cold water. Separate the precipitate, wash with water and dry in vacuo at 75° C. (Yield: 82 g).

Step F: 2-Cyano-6H-6-oxo-dibenz[b,e][1,4]oxathiepin

Stir together at room temperature overnight 8.4 g of the nitrile of Step E and 19.16 g (3 molar equivalents) of dicyclohexylcarbodiimide in 400 ml of ethyl acetate. Filter the reaction mixture to remove the urea. Strip the filtrate to dryness. Triturate the residue in a small volume of ethyl acetate and filter. (Yield 5.5 g purple solid).

Strip the filtrate to dryness and chromatograph on a column of silica gel, eluting with benzene. (Yield 2.1 g white solid), (yield total: 7.6 g).

Step G: 3-(o-Hydroxymethylphenylthio)-4-hydroxybenzonitrile

Dissolve 31.24 g (0.123 mole) of the nitrile of Step F in 750 ml of tetrahydrofuran and add 10.4 g (0.274 moles) of sodium borohydride. Stir the solution at room temperature for 1½ hours. Add water in small portions until foaming ceases. Remove the tetrahydrofuran by evaporation. Shake the residue with ethyl acetate, water and dilute hydrochloric acid. Separate the organic phase and extract the aqueous phase three times with ethyl acetate. Wash the combined organic phases with two small volumes of water, dry and strip to a thick oil which solidifies. (Yield: 39 g).

Step H: 2-Cyano-6H-dibenz[b,e][1,4]oxathiepin

Stir the crude nitrile of Step F(assumed 100% yield, 0.123 mole) and 38 g (50% excess) of dicyclohexylcarbodiimide at 105°–110° C. for 1½ hours. Cool the reaction mixture and extract with methylene chloride. Filter to remove the dicyclohexyl urea and strip the filtrate to dryness. Triturate in a small volume of ethyl acetate, filter and strip to dryness. Extract four times with hot benzene and strip the combined extracts to dryness. Chromatograph on a silica gel column, eluting with benzene to obtain the title product. (m.p. 145°–147° C.).

EXAMPLE 10

6H-Dibenz[b,e][1,4]oxathiepin-2-carboxylic acid

Reflux 3.2 g of the nitrile of Example 9 for 5 hours in a mixture of 50 ml of 20% sodium hydroxide and 50 ml of ethanol. Allow the resulting clear solution to stand at room temperature overnight. Evaporate the ethanol. Dilute the residue with 200 ml of water and heat on a steam bath to dissolve. Filter and acidify the filtrate. Separate the precipitate, wash and dry in vacuo at 75° C. to obtain the title product. (m.p. 225°–227° C.).

EXAMPLE 11

6H-Dibenz[b,e][1,4]oxathiepin-2-carboxylic acid 11-oxide

Suspend 2 g of the acid of Example 10 in 70 ml of acetic acid and add 7 ml of 30% hydrogen peroxide. Heat at 55° C. for 2½ hours. Cool the reaction mixture to room temperature. Separate the precipitate, wash with acetic acid and dry. Dissolve the product in 150 ml of boiling tetrahydrofuran and filter. Concentrate the filtrate to 50 ml. Cool and separate the precipitate to obtain the title product. (m.p. 284°–286° C. slow dec.).

EXAMPLE 12

6H-Dibenz[b,e][1,4]oxathiepin-2-carboxylic acid 11,11-Dioxide

Suspend 1.3 g of the acid of Example 10 in 50 ml of glacial acetic acid and add 7 ml of 30% hydrogen peroxide. Heat slowly to 75° C. and stir for 5 hours. Allow the reaction mixture to stand at room temperature overnight. Separate the precipitate, wash with acetic acid and dry to obtain the title product. (m.p. 279°–282° C.).

EXAMPLE 13

2-Hydroxymethyl-6H-dibenz[b,e][1,4]oxathiepin-11,11-dioxide 725 mg (2.5 mmoles) of the acid prepared in Preparative Example 12, above were dissolved, in 25 ml THF, and there was added 303 mg triethylamine (3 mmoles). The resulting solution was cooled in an ice and water bath, then 298 mg ethyl chloroformate (2.75 mmoles) was added slowly; there was precipitation of $Et_3N \cdot HCl$. The suspension was stirred in the cold for 5 minutes, then there was added 95 mg $NaBH_4$ (2.5 mmoles) and, slowly, 1 ml water; the mixture frothed gently. After stirring for 1 hour in the cold, the cooling bath was removed and the mixture allowed to warm to room temperature and diluted with 5 ml water. The THF was evaporated away and the residual aqueous residue extracted with EtOAc. Extracts were washed with water three times, dried and stripped to a colorless oil containing solids. Thin layer chromatography shows 4–5 spots at this stage. A sample was taken, dissolved in THF and treated with addition of $NaBH_4/H_2O$ and these several spots changed into two; the bulk of the product was given the same treatment after the same workup as before, the crude mixture of two products was chromatographed on silica gel, and a white solid was obtained (most polar compound)triturated in hexane and filtered, which weighed 305 mg, m.p. 148-150, Calc'd: C: 60.85, H: 4.38, S: 11.60. Found: C: 60.91, H: 4.45, S: 11.47.

A sample of this material was tested, and was found that it inhibited the PGEA-induced bronchoconstriction ($R_2$) in the guinea pig in vivo in IV injection, with an $ED_{50}$ of 10.5 mg/kg; on intradermal administration; and also inhibited arachidonic acid induced bronchoconstriction but not induced hypotension in the anaesthetized dog on intraduodenal administration.

EXAMPLE 14

3-(o-Hydroxymethylphenylthio)-4-hydroxybenzoic acid

A mixture of 25 g o-mercaptobenzyl alcohol (0.18 mole), 39.6 g 3-iodo-4-hydroxy benzoic acid (0.15 mole), 11.43 g copper powder (0.18 mole), 70 ml 40% aqueous potassium hydroxide solution (0.5 mole) and 300 ml water was placed under nitrogen atmosphere and stirred under reflux for 18 hours. After cooling the mixture was diluted with 400 ml of water and extracted twice with 100 ml of ethyl acetate to remove neutral products. The aqueous fraction was filtered and the filtrate acidified with conc. HCl to afford the title compound as an oil which solidified and was filtered. There was obtained 32.8 g solid.

EXAMPLE 15

Methyl 3-(o-hydroxymethylphenylthio)-4-hydroxybenzoate 32.5 g of the acid prepared in Example 14 was refluxed in 1000 ml methanol containing 1 ml sulfuric acid for 2 days; the methanol was evaporated away and the residue dissolved in 1 liter of ethyl acetate and the solution washed with water, 10% aqueous sodium bicarbonate solution and water again, dried over sodium sulfate and evaporated to an oil which crystallized on standing, 34 g.

EXAMPLE 16

Methyl 6H-dibenz[b,e][1,4]oxathiepin-2-carboxylate

The 34 g ester from Example 15 (0.111 mole) was dissolved in 650 ml tetrahydrofuran, and there was added 23.4 g diethylazodicarboxylate (0.134 mole); the resulting solution was cooled to 0° C., and a solution of 32.3 g triphenylphosphine (0.123 mole) in 250 ml tetrahydrofuran was added dropwise. The resulting solution was stirred in the cold for an additional 30 minutes. The solvent was evaporated away and to the residue was added 700 ml carbon tetrachloride. The mixture was stirred at room temperature for 30 minutes then the insolubles were filtered and the filtrate evaporated down to an oil which was crude title product and which was hydrolyzed as such without further purification.

EXAMPLE 17

6H-Dibenz[b,e][1,4]oxathiepin-2-carboxylic acid

The crude ester from Example 16 was refluxed gently in a mixture of 500 ml 20% aqueous sodium hydroxide solution and 500 ml tetrahydrofuran for 16 hours. After cooling, the layers were separated; the organic layer was evaporated down, and the residue diluted with 1 liter of water. Insolubles were filtered, and the filtrate was extracted twice with ethyl acetate, then it was acidified with concentrated HCl, affording on filtration 23 g of the crude title compound. This was heated on a steam bath with 280 ml glacial acetic acid, and the mixture filtered while hot. The filtrate was concentrated to a volume of 100 ml, the resulting suspension heated again for 15 minutes then allowed to cool and stand at room temperature overnight. Filtration afforded 15.9 g purified product, m.p.: 225°–227°.

EXAMPLE 18

2-Hydroxymethyl-6H-dibenz[b,e][1,4]oxathiepin

Dissolve 10 mmoles of 6H-dibenz[b,e][1,4]oxathiepin-2-carboxylic acid from Example 17 in 75 ml tetrahydrofuran, add slowly at ambient temperature 12 ml of a 1 molar solution of borane in tetrahydrofuran, stir for 3 hours, add 20 ml water, evaporate the tetrahydrofuran, dilute the residue with water and filter. Crystallize the crude product from ethanol.

EXAMPLE 19

2-Hydroxymethyl-6H-dibenz[b,e][1,4]oxathiepin-11-oxide

Reduce 6H-dibenz[b,e][1,4]oxathiepin-2-carboxylic acid-11-oxide from Example 11 with borane in THF as in Example 15 to obtain the corresponding alcohol.

EXAMPLE 20

2-Hydroxymethyl-6H-dibenz[b,e][1,4]oxathiepin-11,11-dioxide 6.50 g sulfone acid from Example 12 (22.4 mmoles) were dissolved in 150 ml tetrahydrofuran; to this solution at room temperature there was added slowly 40 ml of a 1.1 molar solution of borane in tetrahydrofuran. The mixture was stirred at room temperature for 3 ½ hours, then there was added slowly 25 ml water. The tetrahydrofuran was evaporated away, the remaining aqueous residue contained the crude product as an oily deposit which slowly solidified. It was collected by filtration and crystallized from ethanol. The yield was 4.50 g, m.p.: 148°–149°.

EXAMPLE 21

2-Acetoxymethyl-6H-dibenz[b,e][1,4]oxathiepin-11,11-dioxide

A mixture of 2-hydroxymethyl-6H-dibenz[b,e][1,4]oxathiepin-11,11-dioxide (200 mg), pyridine (1 ml) and acetic anhydride (0.25 ml) was stirred at room temperature for 30 minutes. The excess of reagents was evaporated under reduced pressure. The solid residue was triturated with hexane and filtered to afford the title compound (220 mg) as a white solid, m.p.: 149°–151°.

EXAMPLE 22

2-Acetoxymethyl-6H-dibenz[b,e][1,4]oxathiepin-11-oxide

Using the procedure of Example 21, substituting 2-hydroxymethyl-6H-dibenz[b,e][1,4]oxathiepin-11-oxide for the corresponding 5,5-dioxide, to obtain the title compound.

EXAMPLE 23

2-Acetoxymethyl-8-fluoro-6H-dibenz[b,e][1,4]oxathiepin-11-oxide

Using the procedure of Example 21, substituting 8-fluoro-2-hydroxymethyl-6H-dibenz[b,e][1,4]oxathiepin-11-oxide for 2-hydroxymethyl-6H-dibenz[b,e][1,4]oxathiepin-5,5-oxide, to obtain the title compound.

EXAMPLE 24

2-Acetoxymethyl-8-fluoro-6H-dibenz[b,e][1,4]oxathiepin-11,11-dioxide

Using the procedure of Example 21, substituting 8-fluoro-2-hydroxymethyl-6H-dibenz[b,e][1,4]oxathiepin-11,11-dioxide for 2-hydroxymethyl-6H-dibenz[b,e][1,4]oxathiepin-11,11-dioxide, to obtain the title compound.

EXAMPLE 25

2-Acetoxymethyl-9-fluoro-6H-dibenz[b,e][1,4]oxathiepin-11-oxide

Using the procedure of Example 21, substituting 9-fluoro-2-hydroxymethyl-6H-dibenz[b,e][1,4]oxathiepin-11-oxide for 2-hydroxymethyl-6H-dibenz[b,e][1,4]oxathiepin-11,11-dioxide, to obtain the title compound.

EXAMPLE 26

2-Acetoxymethyl-9-fluoro-6H-dibenz[b,e][1,4]oxathiepin-11,11-dioxide

Using the procedure of Example 21, substituting 9-fluoro-2-hydroxymethyl-6H-dibenz[b,e][1,4]oxathiepin-11,11-dioxide for 2-hydroxymethyl-6H-dibenz[b,e][1,4]oxathiepin-11,11-dioxide, to obtain the title compound.

EXAMPLE 27

9-Acetoxymethyl-6H-dibenz[b,e][1,4]oxathiepin-11,11-dioxide

Using the procedure of Example 21, substituting 9-hydroxymethyl-6H-dibenz[b,e][1,4]oxathiepin11,11-dioxide for 2-hydroxymethyl-6H-dibenz[b,e][1,4]oxathiepin-11,11-dioxide, to obtain the title compound.

EXAMPLE 28

9-Fluoro-2-hydroxymethyl-6H-dibenz[b,e][1,4]oxathiepin-11,11-dioxide

Step A: Bis-(2-carboxy-5-nitrophenyl)disulfide

2-Amino-4-nitrobenzoic acid (18 g, 0.1 mole) was added to water (90 ml) and the mechanically stirred slurry was placed in an ice and water bath; there was then added slowly sulfuric acid (30 ml over about 10 min) so that the temperature did not go over 25°; solution did not occur, but the mixture became less viscous; this suspension was cooled down to 5° and stirred at that temperature for 20 minutes. Then there was begun the slow addition of a solution of sodium nitrite (11.7 g, 0.166 mole) in water (18 ml). The addition was done in small portions over 1 hour, each portion added beneath the surface of the mixture. Toward the end of the addition, frothing occurred. After the addition the mixture was stirred for a further 1 ½ hour at 0°. The mixture was filtered and the filtrate kept cold. The cold filtrate was added dropwise to a solution of sodium carbonate (100 g) and ethyl xanthic acid potassium salt (18 g) in water (750 ml) preheated to 50° in an oil bath. The displacement of the diazonium salt was immediate as each drop caused gassing. The resulting red solution was heated up to 70° (internal) and stirred at that temperature for 3 hours. There was then added more $Na_2CO_3$ (25 g) and the heating and stirring was continued for 2 ½ hours. The mixture was allowed to cool to room temperature and stirred overnight.

A small amount of solid had separated and it was filtered off. The filtrate was acidified slowly with conc. HCl affording a sticky solid which was filtered. The crude product was heated in about 40 ml acetic acid on a steam bath for about ½ hour, then the mixture was allowed to cool and stir at room temperature overnight.

The insolubles were filtered, yielding an orange solid, 11.76 g.

The crude orange product was dissolved in about 500 ml boiling acetone. The mixture was filtered hot and concentrated until crystallization began. The mixture was allowed to cool down and stand for a few hours, then filtered, to afford the title compound (44 g) as an orange solid.

Step B: 2-Mercapto-4-nitrobenzyl alcohol

The compound of Step A above (9.50 g, 24 mmoles) was dissolved in THF (100 ml) and the mixture placed under $N_2$ atmosphere. There was added slowly an approximately 1.1M $BH_3$/THF solution (50 ml) and the mixture stirred at room temperature overnight. The mixture had become a slurry containing a gelatinous solid. There was next added additional $BH_3$ solution (25 ml) and after 3 hours the solids had dissolved partly and TLC showed a mixture of I and II. Additional borane solution (25 ml) was added and the mixture stirred overnight at room temperature. A clear amber solution had formed and TLC showed only product and a new less polar spot. There was added carefully, water (50 ml) and the THF was evaporated away leaving a yellow solid and the aqueous fraction. This was partitioned between EtOAc and in $Na_2CO_3$. The organic layer continued the unknown side-product, I, and the aqueous phase contained the title compound, II. Acidification and extraction with EtOAc afforded II as a yellow solid, 3.07 g.

Step C: 3-(2-Hydroxymethyl-5-nitrophenylthio)-4-hydroxybenzoic acid

A mixture of 2-mercapto-4-nitrobenzyl alcohol (3.49 g, 18.86 mmoles), 4-hydroxy-3-iodo-benzoic acid (4.67 g, 17.69 mmoles), red cuprous oxide (1.35 g, 9.44 mmoles) and 1-methyl-2-pyrrolidinone (40 ml) was heated under a $N_2$ atmosphere. The mixture became a thick slurry at about 90° but at 130° had become a dark red solution. After ½ hour at 140° TLC showed that the reaction was finished. The mixture was poured onto 2N HCl (200 ml) and after stirring for a few minutes it was extracted 4× with EtOAc. The EtOAc extracts were washed with water, then extracted 4× with 1N NaOH. The aqueous extracts were washed once with EtOAc then acidified and the resulting solid filtered, washed with water and dried to yield 4.65 g of the title compound.

Step D: Methyl 3-(2-hydroxymethyl-5-nitrophenylthio)-4-hydroxy benzoate

The crude acid from Step C above (4.65 g) was refluxed with methanol (250 ml) containing $H_2SO_4$ (5 ml). After 5 hours TLC showed no more acid present. The methanol was evaporated away almost completely and there was added water (25 ml) and, carefully, there was added solid $NaHCO_3$ until all of the acid had been neutralized. The ester was extracted into EtOAc (3×) and the combined organics washed with water (3×), dried over $Na_2SO_4$ and evaporated to yield the title compound as a brown solid (4.54 g).

Step E: Methyl 9-nitro-6H-dibenz[b,e][1,4]oxathiepin-2-carboxylate

The ester from Step D above (4.54 g, 13.55 mmoles) was dissolved in THF (100 ml) and there was added diethylazodicarboxylate (3.0 g, 16.4 mmoles); the solution was cooled in an ice and water bath, and there was added slowly a solution of triphenylphosphine (4.25 g, 16.22 mmoles) in THF (30 ml). After the addition, the mixture was stirred in the cold for 15 minutes and the cooling bath was removed. When the temperature had risen to room temperature, TLC showed that the reaction was over, but stirring was continued overnight. The mixture was evaporated to dryness and the residue dissolved in boiling EtOAc (100 ml). The mixture was concentrated to about 70 ml by boiling away the solvent. Then the mixture was allowed to cool down to room temperature. After 4 hours the crystalline material was filtered and dried affording the title compound as a yellow fluffy solid. m.p.: 178°–179°. The filtrate was stripped down and the residue dissolved in $CH_2Cl_2$ and chromatographed on a column of silica gel, eluting with $CH_2Cl_2$; there was obtained 1.2 g of the title compound contaminated with a small amount of more polar material. This was crystallized from EtOAc and there was obtained 0.73 g of the title compound.

Step F: Methyl 9-amino-6H-dibenz[b,e][1,4]oxathiepin-2-carboxylate

The ester from Step E above (2.83 g, 8.93 mmole) was suspended in THF (40 ml) and conc. HCl (8 ml) was added. Next was added stannous chloride dihydrate (6.63 g, 23 mmoles). The mixture was stirred at room temperature overnight. The reaction was not complete so additional stannous chloride (2 g) was added and stirring was continued for 7 hours, whereupon TLC showed completeness of the reduction. The mixture was diluted witn 1N NaOH (100 ml) and EtOAc. The presence of tin salts made extraction difficult so they were filtered through a bed of Celite. The organic extracts (3×) were washed with saturated NaCl solution twice, then dried over $Na_2SO_4$ overnight. The solution was then evaporated to an oil (about 8 g). Addition of water caused separation of an orange solid which was filtered, washed with water and dried hydrochloride to yield the title compound, m.p.: >200°. The original tin salt and Celite residues were found to contain product; not enough base had been used. They were suspended in 1N NaOH (100 ml) extracted again with EtOAc. The extracts washed with water, dried over $Na_2SO_4$, stripped down to an orange solid which was titrated with water and filtered. The solid was dried affording 1.55 g of the title compound, m.p. 155°–157°.

Step G: Methyl 9-fluoro-6H-dibenz[b,e][1,4]oxathiepin-2-carboxylate

The amino ester from Step F above (1.45 g, 5.05 mmoles) was suspended in conc. HCl (21 ml) and the mixture stirred vigorously for 10 minutes at room temperature, then cooled in an ice, salt and water bath. At 5° C. there was begun the addition of a cold solution of sodium nitrite (710 mg, 10.3 mmole) in water (5 ml). This addition was done over about 10 minutes, the solution being added in portions below the surface of the reaction mixture. After the addition, the frothing mixture was stirred in the cold for a further 10 minutes then there was added 48% fluoroboric acid (21 ml) precooled. This caused separation of a yellow solid. The suspension was stirred in the cold for 15 minutes then the solid was filtered, washed with cold 24% $HBF_4$ solution and air dried overnight. The slightly damp solid was added portionwise to decalin (15 ml) preheated to 100°. Each addition of a portion caused frothing; after the addition the mixture was stirred at 100° for a further 20 minutes, then the liquid portion was decanted and the insolubles extracted twice with boiling toluene (10 ml). The combined extracts and original decalin solution was cooled and injected as such as a column of silica gel (about 100 g) packed in toluene. Elution with toluene afforded the title compound as a white solid, 310 mg, m.p.: 131°–132° C.

Step H: 9-Fluoro-6H-dibenz[b,e][1,4]oxathiepin-2-carboxylic acid

The ester from Step G above (395 mg) at 50°–55° C. in a mixture of 20% aqueous NaOH (10 ml) and DAG-ethanol (10 ml) for 2 hours. The mixture was concentrated to about ½ volume, diluted with water (20 ml). The solids (Na salt of acid) did not dissolve even on warming. The warm mixture was stirred and acidified with 20% aqueous HCl. The resulting suspension was stirred for 20 minutes at room temperature to afford the title compound as a white solid.

Step I: 9-Fluoro-2-hydroxymethyl-6H-dibenz[b,e][1,4]oxathiepin

The acid from Step H above (320 mg) was dissolved in THF (15 ml) and at room temperature under $N_2$ atmosphere, there was added slowly a 1.04 M solution of borane-THF (3 ml). The mixture was stirred at room temperature for 4 hours, then, slowly there was added water. The THF was evaporated away and the solid residue triturated in water, filtered and dried to yield the title compound (285 mg) as a white solid, m.p. 116°–117° C.

Step J: 9-Fluoro-2-hydroxymethyl-[b,e][1,4]oxathiepin-11,11-dioxide

The alcohol of Step I above (200 mg) was dissolved in methylene chloride (10 ml) and there was added m-chloroperbenzoic acid (411 mg). The reaction mixture was stirred overnight at room temperature. There was added $Ca(OH)_2$ (1 g) and after stirring for 10 minutes the mixture was filtered through Celite and the filtrate evaporated to an oily residue which was chromatographed on a column of silica gel, eluting with 20% ethyl acetate/toluene. The title product thus obtained was crystallized from toluene-hexane affording white fluffy crystals, m.p.: 106°–107° C., Calc'd: C: 57.13, H: 3.77, S: 10.90, F: 6.46.
Found: C: 57.12, H: 3.88, S: 10.98, F: 6.49.

EXAMPLE 29

8-Fluoro-2-hydroxymethyl-6H-dibenz[b,e][1,4]oxathiepin-11,11-dioxide

Following the procedure of Example 28, Steps A–F, starting with 2-amino-5-nitrobenzoic acid, there was obtained:

Step A: 15.72 g of bis-(2-carboxy-4-nitrophenyl)disulfide
Step B: 3.1 g of 2-mercapto-5-nitrobenzyl alcohol
Step C: 4.07 g of 3-(2-hydroxymethyl-4-nitrophenylthio)-4-hydroxy benzoic acid
Step D: 2.64 g of methyl 3-(2-hydroxymethyl-4-nitrophenylthio)-4-hydroxy benzoate, m.p. 180°–183° C.
Step E: 6.15 g of methyl 8-nitro-6H-dibenz[b,e][1,4]oxathiepin-2-carboxylate, m.p. 225°–226° C.
Step F: 144 mg of methyl 8-amino-6H-dibenz[b,e][1,4]oxathiepin-2-carboxylate, m.p. 154°–155° C.
Step G: Methyl 8-diazo-6H-dibenz[b,e][1,4]oxathiepin-2-carboxylate fluoroborate The amino ester from Step F above (780 mg, 2.72 mmoles) was suspended in conc. HCl (10 ml) and the mixture was stirred vigorously at room temperature for 10 minutes. The solid had become a fine suspension.

The mixture was cooled in an ice and salt bath and at 0° there was added slowly (over about 10 minutes) a cold solution of sodium nitrite (540 mg, 7.83 mmoles) in water (1.5 ml). The mixture turned red-orange and the solids dissolved almost completely, then a new orange solid separated out. The mixture was stirred at ≦0° C. for 15 minutes then there was added dropwise (10 ml) pre-cooled 48% fluoroboric acid (10 ml). The orange solid became yellow and the resulting suspension was stirred in the cold for 1 hour, then filtered, washed with cold 25% $HBF_4$ solution and air dried overnight affording the title compound (1.46 g) as a yellow solid.

Step H: Methyl 8-fluoro-6H-dibenz[b,e][1,4]oxathiepin-2-carboxylate

The crude diazonium salt from Step G above (1.31 g) was placed in a 50 ml flask, immersed in an oil bath preheated to 105° and a slight vacuum was applied. Within a few moments the solid began to melt and evolve gas. Heating was continued for 20 minutes, then the mixture was cooled and dissolved in THF (all soluble); there was added 5 grams of silica gel, the mixture evaporated to dryness and the solids placed atop a column of 50 g silica gel. Elution with toluene afforded the title compound (170 mg) as a yellow solid, m.p.: 119°–121° C.

Step I: 8-Fluoro-6H-dibenz[b,e][1,4]oxathiepin-2-carboxylic acid

The ester from Step H above (200 mg) was stirred at room temperature in a mixture of 20% aqueous NaOH (10 ml) and THF (10 ml) overnight. Very little hydrolysis had occurred. The mixture was brought to reflux. After 6 hours refluxing was stopped; TLC showed mostly product and a residual less polar spot (weak) which seemed to be very slightly different from the starting ester. The biphasic mixture containing solids was allowed to stir at room temperature overnight. The mixture was diluted with water and EtOAc. The aqueous fraction was collected, leaving behind the organic layer and solids. The organic phase was extracted with water and the solids dissolved. The aqueous phases were combined. Source solids came out of solution. The aqueous suspension was warmed on a steam bath to about 50°, then acidified with concentrated HCl. A fluffy white solid came out. The suspension was cooled down to room temperature and filtered. The solid was washed with water and dried affording the title compound (90 mg), m.p.: 278°–280° C.

Step J: 8-Fluoro-2-hydroxymethyl-6H-dibenz[b,e][1,4]oxathiepin

The compound of Step I above (110 mg, 0.4 mmole) was dissolved in THF (5 ml) and there was added a 1.1M solution of borane in THF (1 ml). The mixture was stirred at room temperature. After ½ hour, a TLC was taken and showed a 1:1 mixture of product and starting material. After 4 hours the reduction was complete. There was then added carefully a few ml's of water and the THF was evaporated away. The residual aqueous mixture contained a white solid. After dilution with $H_2O$ the solid was filtered to yield the title compound (87 mg), m.p.: 124°–125° C.

Step K: 8-Fluoro-2-hydroxymethyl-6H-dibenz[b,e][1,4]oxathiepin-11,11-dioxide

The compound from Step J above (85 mg, 0.324 mmole) was dissolved in $CH_2Cl_2$ (7–8 ml) and there was added m-chloroperbenzoic acid (203 mg, 1 mmole). The mixture was stirred at room temperature overnight. There was then added calcium hydroxide (0.5 g), the mixture was stirred for 10 minutes and then filtered through a bed of Celite. The filtrate was evaporated and the residue was chromatographed on a column of silica gel, eluting with 20% ethyl acetate/toluene. Pertinent fractions were stripped down to a solid residue (90 mg) which was swirled with hexane, then the hexane removed by decantation. After evaporation of residual hexane the title compound was obtained, m.p.: 146°–148° C.

EXAMPLE 30

Following the procedures of Examples 28 and 29, the compounds 2-hydroxymethyl-8-(or 9-)bromo, chloro or iodo-6H-dibenz[b,e][1,4]oxathiepin, and the 11-oxide or 11,11-dioxide derivatives are made in a similar manner. The starting reactants are 3-iodo-4-hydroxybenzoic acid and 2-mercapto-4-(or 5-) nitrobenzyl alcohol. These reactants are reacted using copper powder in potassium hydroxide solution to form the 3-(2-hydroxymethyl-4-(or 5-) nitrophenylthio)-4-hydroxybenzoic acid. This is converted to the corresponding methyl benzoate, the nitro group is then reduced to an amino group, and the latter transformed to the desired halo compound.

For instance, methyl 8-(or 9-) fluoro-6-H-dibenz[b,e][1,4]oxathiepin-2-carboxylate is prepared using fluoroboric acid and sodium nitrite in a diazotization reaction. When the diazotization reaction described above is performed using sulfuric acid instead of fluoroboric acid, and the resulting diazonium salt added to a solution of cuprous chloride, cuprous bromide, or potassium iodide, in aqueous hydrochloric acid, the corresponding compound methyl 8-(or 9-) chloro, bromo or iodo-6H-dibenz[b,e][1,4]oxathiepin-2-carboxylate is obtained.

These esters are then treated with aqueous sodium hydroxide, and methanol to form the corresponding 2-carboxylic acid.

These 2-carboxylic acids are then reduced to the corresponding 2-hydroxymethyl compounds.

Following analogous reactions described above, the compounds 2-hydroxymethyl-8(or 9)-chloro, bromo or iodo-6H-dibenz[b,e][1,4]oxathiepins are obtained.

These can be analogously transformed into the compounds:

2-hydroxymethyl-8-(or 9)-chloro, bromo or iodo-6H-dibenz[b,e][1,4]oxathiepin-11-oxide; and 2-hydroxymethyl-8-(or 9)-chloro, bromo or iodo-6H-dibenz[b,e][1,4]oxathiepin-11,11-dioxide.

EXAMPLE 31

The compounds 2-(or 3)-chloro, bromo, fluoro-or-iodo-9-hydroxymethyl-6H-dibenz[b,e][1,4]oxathiepin and the 11-oxide and 11,11-dioxide derivatives are similarly prepared, starting with a reaction between 4-(or 5)-fluoro, chloro, bromo, or iodo-2methoxythiophenol and 2-chloro-4-nitro benzoic acid.

Some of the compounds of formulae I and IA are capable of existing as optical isomers which may be resolved by known procedures into their enantiomers. Each of the enantiomorphic isomers may exhibit variation in biological potency.

What is claimed is:

1. A compound of the formulae:

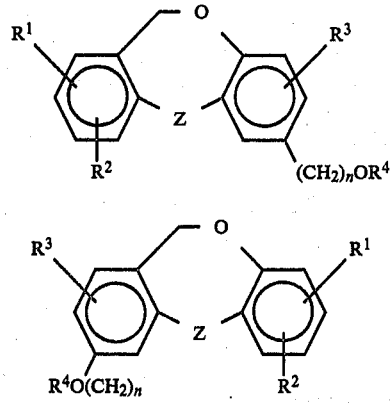

wherein
n is an integer from 1 to 4;
Z is thio, sulfinyl, or sulfonyl;
$R^1$, $R^2$ and $R^3$ are each independently selected from hydrogen, halogen, amino, $C_1$ to $C_4$ alkyl, $C_1$ to $C_4$ alkylthio, $C_1$ to $C_4$ alkylsulfinyl, $C_1$ to $C_4$ alkylsulfonyl, trifluoromethyl, trifluoromethylthio, cyano, nitro, and $C_1$ to $C_4$ alkylamino, $C_1$ to $C_4$ dialkylamino, $C_1$ to $C_4$ alkoxy, $C_1$ to $C_4$ alkanoyl, aralkyl, or hydroxy $C_1$ to $C_4$ alkyl;
$R^4$ is H, $C_1$ to $C_4$ acyl, $C_1$ to $C_4$ alkylaminoacyl, $C_1$ to $C_4$ alkylcarboxy, $C_1$ to $C_4$ alkylcarboxamido, $C_1$ to $C_4$ alkylcarboxamidoacyl or $C_1$ to $C_4$ acyloxy $C_1$ to $C_4$ alkyl;
$R_1$ and $R_2$ can also be a $C_2$ to $C_6$ polymethylene chain optionally with a hydroxy or keto functionality.

2. A compound according to claim 1 where Z is sulfonyl, n is 1, $R^2$ and $R^3$ are hydrogen, and $R^1$ is fluoro, chloro, bromo, or amino at the 8- or 9- position in structure I or at the 2- or 3-position in structure IA.

3. The compounds of claim 1: 9-hydroxymethyl-6H-dibenz[b,e][1,4]oxathiepin 11,11-dioxide; 9-hydroxymethyl-6H-dibenz[b,e][1,4]oxathiepin; 9-hydroxymethyl-6H-dibenz[b,e][1,4]oxathiepin-11-oxide; 2-hydroxymethyl-6H-dibenz[b,e][1,4]oxathiepin-11,11-dioxide; 2-hydroxymethyl-6H-dibenz[b,e][1,4]oxathiepin; 2-hydroxymethyl-6H-dibenz[b,e][1,4]oxathiepin-11-oxide; 2-hydroxymethyl-6H-dibenz[b,e][1,4]oxathiepin-11,11-dioxide; 2-acetoxymethyl-6H-dibenz[b,e][1,4]oxathiepin-11-oxide; 2-acetoxymethyl-6H-dibenz[b,e][1,4]oxathiepin-11,11-dioxide; 2-acetoxymethyl-8-fluoro-6H-dibenz[b,e][1,4]oxathiepin-11-oxide; 2-acetoxymethyl-8-fluoro-6H-dibenz[b,e][1,4]oxathiepin-11,11-dioxide; 2-acetoxymethyl-9-fluoro-6H-dibenz[b,e][1,4]oxathiepin-11-oxide; 2-acetoxymethyl-9-fluoro-6H-dibenz[b,e][1,4]oxathiepin-11,11-dioxide; 9-acetoxymethyl-6H-dibenz[b,e][1,4]oxathiepin-11,11-dioxide; 9-fluoro-2-hydroxymethyl-6H-dibenz[b,e][1,4]oxathiepin-11,11-dioxide; 9-fluoro-2-hydroxymethyl-6H-dibenz[b,e][1,4]oxathiepin; 8-fluoro-2-hydroxymethyl-6H-dibenz[b,e][1,4]oxathiepin-11,11-dioxide; 8-fluoro-2-hydroxymethyl-6H-dibenz[b,e][1,4]oxathiepin.

4. The compound of claim 1 which is: 2-Hydroxymethyl-6H-dibenz[b,e][1,4]oxathiepin-11,11-dioxide.

5. The compound of claim 1 which is: 8-fluoro-2-hydroxymethyl-6H-dibenz[b,e][1,4]oxathiepin-11,11-dioxide.

6. The compound of claim 1 which is: 9-fluoro-2-hydroxymethyl-6H-dibenz[b,e][1,4]oxathiepin-11,11-dioxide.

7. The compound of claim 1 which is: 9-hydroxymethyl-6H-dibenz[b,e][1,4]oxathiepin11,11-dioxide.

8. The compound of claim 1 which is: 2-fluoro-9-hydroxymethyl-6H-dibenz[b,e][1,4]oxathiepin-11,11-dioxide.

9. The compound of claim 1 which is: 3-fluoro-9-hydroxymethyl-6H-dibenz[b,e][1,4]oxathiepin-11,11-dioxide.

* * * * *